United States Patent [19]

Liebert et al.

[11] Patent Number: 5,207,983

[45] Date of Patent: May 4, 1993

[54] METHOD OF TERMINAL STEAM STERILIZATION

[75] Inventors: Richard T. Liebert, Ballston Spa; Neil H. Brown, Nassau; John R. Pistolese, Valatie, all of N.Y.

[73] Assignee: Sterling Winthrop Inc., New York, N.Y.

[21] Appl. No.: 827,239

[22] Filed: Jan. 29, 1992

[51] Int. Cl.[5] .................................... A61L 2/00
[52] U.S. Cl. ........................................ 422/25; 422/26
[58] Field of Search ............... 422/25, 26, 295, 307; 604/232–235, 187, 218

[56] References Cited

U.S. PATENT DOCUMENTS

| | | | |
|---|---|---|---|
| 3,086,837 | 4/1963 | Wilkinson et al. | 422/25 |
| 3,270,483 | 6/1966 | Smoyer et al. | 422/25 |
| 3,468,471 | 9/1969 | Linder | 53/486 |
| 3,705,582 | 12/1972 | Stumpf et al. | 604/49 |
| 4,406,861 | 9/1983 | Beauvais et al. | 422/26 |
| 4,457,327 | 7/1984 | Pepper | 422/112 |
| 4,673,396 | 6/1987 | Urbaniak | 604/187 |
| 4,718,463 | 1/1988 | Jurgens et al. | 422/25 |
| 4,834,717 | 5/1989 | Haber et al. | 604/232 |

FOREIGN PATENT DOCUMENTS 2524079 12/1975 Fed. Rep. of Germany ........ 422/26

1544260 4/1979 United Kingdom .................. 422/26

Primary Examiner—Robert J. Warden
Assistant Examiner—Hien Tran
Attorney, Agent, or Firm—Imre (Jim) Balogh; Arthur Rosenstein

[57] ABSTRACT

Disclosed is a method for terminal steam sterilization of a pre-filled plastic syringe or a pre-filled plastic cartridge, said method comprising the steps of: maintaining a head space in the syringe or cartridge of less than about 10%—of the fill—volume; providing at least a 10% leeway for the plunger therein to slide in response to pressure differential; and sterilizing the syringe or cartridge at an autoclave pressure that is less than the internal pressure of the syringe or cartridge.

Also disclosed is a method for terminal steam sterilization of a pre-filled glass syringe or pre-filled glass cartridge, said method comprising the steps of: maintaining a head space in the syringe or cartridge of less than about 10%—of the fill—volume; providing at least a 10% leeway for the plunger therein to slide in response to pressure differential; and sterilizing the glass syringe or glass cartridge at an autoclave pressure that is less than, equal to or greater than the internal pressure of the syringe or cartridge.

30 Claims, 3 Drawing Sheets

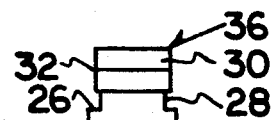
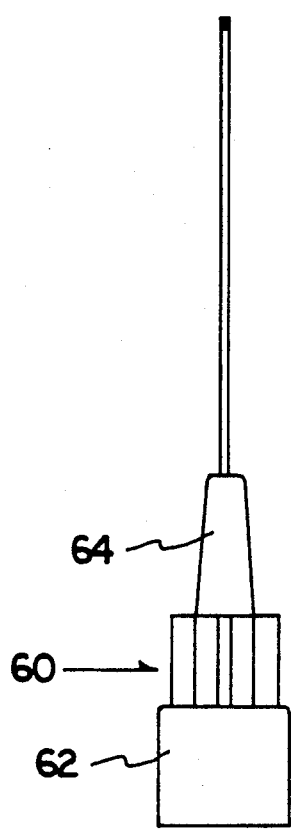
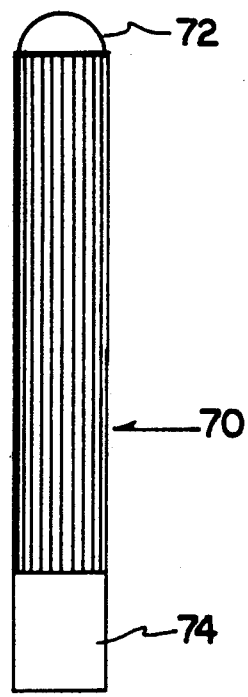
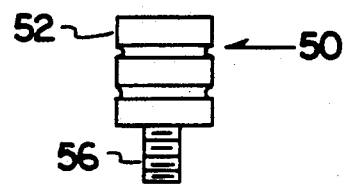

METHOD OF TERMINAL STEAM STERILIZATION

BACKGROUND OF THE INVENTION

1. Field of the Invention

The present invention relates to a process for terminal sterilization of pre-filled plastic and glass syringes and cartridges containing liquid pharmaceutical, biological or veterinary products. More particularly, the invention relates to a process for terminal sterilization of liquid contrast media for parenteral administration contained in plastic and glass syringes and cartridges.

2. Reported Developments

The prior art discloses containers, apparatus and processes for steam-sterilization of products and medical devices used in the health and medical fields where sterility is an absolute requirement. Generally speaking, such sterilization may be accomplished by steam-sterilizing the containers/packages and contents separately, followed by placing the contents into the containers/packages and hermetically sealing the same for use at a later time. Such processes, however, carry the risk of contamination and introduction of pyrogens during the transfer of the products into their containers/packages. The trend in the pharmaceutical industry is toward terminal steam-sterilization wherein the contents are sterilized within their containers/packages.

In the process of steam-sterilization, the pre-filled containers/packages are placed in an autoclave and are subjected to operational cycles which include: purging air from the autoclave chamber by forcing saturated steam therethrough at about a pressure of 1 to 20 psig at a temperature of about 100° C. to 150° C. for about a minute to 30 minutes; further introducing steam into the autoclave chamber so that the temperature of about 100° C. to 125° C. is reached therein; maintaining the temperature for a time sufficient to sterilize the content of the autoclave; cooling the autoclave and removing the containers/packages therefrom. Typical containers containing parenteral formulations, such as glass ampules, stoppered vials and bottles are able to withstand the pressure differentials between the containers and the autoclave chamber created by the operational cycles of the sterilization process. However, pre-filled syringes and cartridges made of plastic or glass do not tolerate significant pressure differential when the internal pressure is greater than the external; such pressure differential results in an unacceptable number of container/package failures that will occur either during the heating phase or the cooling phase of the autoclave cycle.

In the case of glass syringes and cartridges such failure typically will be in the form of plunger blow-out during the heating phase caused by the sum total of product vapor pressure, thermal expansion of the product and the pressure increase of the gas occupying the head space in the container. Should seal integrity be maintained through the heating phase, failure may occur during the cool-down phase of the sterilization cycle when the liquid content in the containers is at or above its boiling point, creating pressures within the containers greater than one atmosphere while the pressure in the autoclave drops to one atmosphere.

In the case of plastic syringes and cartridges, in addition to container/package failure by plunger blow-out during sterilization, the heat and pressure in the autoclave chamber soften the plastic and tend to warp and deform the walls of the containers.

The need to compensate for the elevated internal pressure of a plastic syringe during sterilization was recognized in U.S. Pat. No. 4,718,463 which proposes to maintain a pressure in the autoclave chamber at least equal to the pressure inside the syringe.

We have surprisingly found that pre-filled plastic syringes and cartridges may be steam-sterilized by autoclaving without encountering the above-mentioned problems and without the necessity of maintaining the autoclave pressure at or above the internal pressure of the syringes and cartridges and preferably no head space, in the syringes and cartridges; and providing at least 10% empty space between the plunger and the proximal end of the barrel to allow for sliding movement of the plunger toward the proximal end of the barrel in response to internal pressure generated during the autoclaving cycles.

Pre-filled glass syringes and cartridges having the above-described provisions relating to plastic syringes and cartridges may also be steam-sterilized using an autoclave pressure that is less than the internal pressure of the glass syringes and cartridges. However, we have found that they may also be sterilized using overpressure without the danger of plunger blow-out if the head space is minimized and sufficient plunger movement is allowed in the barrel.

SUMMARY OF THE INVENTION

The present invention provides a method for terminal sterilization of a pre-filled plastic syringe containing a liquid, preferably a liquid medicament, for parenteral administration, said syringe comprising:
- a syringe barrel terminating in a nozzle at its distal end, and an open or proximal end; and
- situated in the barrel is a slideable plunger or piston having a means to engage a plunger rod, said method comprises the steps of:
- inserting the plunger into the barrel and sliding it toward the distal end thereof to leave a volume of at least 2% empty space between the plunger and the proximal end of the barrel;
- filling the syringe through its nozzle with the liquid medicament allowing for a head space not exceeding 10% by volume and, preferably, without allowing for head space;
- hermetically sealing the nozzle by a cap;
- autoclaving the pre-filled syringe to sterilize its content at an autoclave pressure less than the pressure inside the syringe; and
- cooling the autoclave chamber with a water cascade or nozzle spray or air draft at a rate that will not allow a sudden collapse of the steam atmosphere in the autoclave chamber.

In another embodiment the present invention provides a method for terminal sterilization of a pre-filled cartridge containing a liquid, preferably a liquid medicament for parenteral administration, said cartridge comprising:
- a cartridge barrel terminating in a neck portion at its distal end adapted to receive a pierceable diaphragm and an open or proximal end; and
- situated in the barrel is a slideable plunger or piston having a means to engage a plunger rod, said method comprises the steps of:
- inserting the plunger into the cartridge barrel and positioning it to leave a volume of at least 2% empty space between the plunger and the proximal end of the cartridge barrel;

filling the cartridge barrel with a liquid medicament through its distal end allowing for a head space; and not exceeding 10% by volume and, preferably, without allowing for head space;

hermetically sealing the distal end by a pierceable diaphragm; and autoclaving the pre-filled cartridge to sterilize the pre-filled cartridge and its content at an autoclave pressure that is less than the pressure inside the cartridge; and cooling the autoclave chamber with a water cascade or nozzle spray or air draft at a rate that will not allow a sudden collapse of the steam atmosphere in the autoclave chamber.

In a further embodiment the present invention provides a method for terminal sterilization of a pre-filled glass syringe containing a liquid, preferably a liquid medicament, for parenteral administration, said syringe comprising:

a syringe barrel terminating in a nozzle at its distal end, and an open or proximal end; and situated in the barrel is a slideable plunger or piston having a means to engage a plunger rod, said method comprises the steps of:

inserting the plunger into the barrel and sliding it toward the distal end thereof to leave a volume of at least 2% empty space between the plunger and the proximal end of the barrel;

filling the syringe through its nozzle with the liquid medicament allowing for a head space not exceeding 10% by volume and, preferably, without allowing for head space;

hermetically sealing the nozzle by a cap;

autoclaving the pre-filled syringe to sterilize its content at an autoclave pressure that is less than, equal to or greater than the pressure inside the syringe; and cooling the autoclave chamber with a water cascade or nozzle spray or air draft at a rate that will not allow a sudden collapse of the steam atmosphere in the autoclave chamber.

In still another embodiment the present invention provides a method for terminal sterilization of a pre-filled glass cartridge containing a liquid, preferably a liquid medicament, for parenteral administration, said cartridge comprising:

a cartridge barrel terminating in a nozzle at its distal end, and an open or proximal end; and situated in the barrel is a slideable plunger or piston having a means to engage a plunger rod, said method comprises the steps of:

inserting the plunger into the barrel and sliding it toward the distal end thereof to leave a volume of at least 2% empty space between the plunger and the proximal end of the barrel;

filling the cartridge through its nozzle with the liquid medicament allowing for a head space not exceeding 10% by volume and, preferably, without allowing for head space;

hermetically sealing the nozzle by a cap;

autoclaving the pre-filled cartridge to sterilize its content at an autoclave pressure that is less than, equal to or greater than the pressure inside the cartridge; and cooling the autoclave chamber with a water cascade or nozzle spray or air draft at a rate that will not allow a sudden collapse of the steam atmosphere in the autoclave chamber.

In practicing the present invention, it is essential to satisfy two requirements: (1) to maintain a head space not exceeding 10% of the fill volume in the syringe or cartridge, and preferably, no head space at all; and (2) to provide sufficient leeway for the plunger to allow movement toward the proximal end of the barrel in response to the thermal expansion of the content in the barrel. When these requirements are met, sterilization of pre-filled plastic syringes and cartridges by saturated steam can be accomplished under an autoclave pressure that is less than the pressure in the syringes and cartridges. In order to prevent the collapse of the steam atmosphere, the rate of cooling should be maintained within one unit of chamber controllability, i.e., the pressure in the chamber should be one psig lower than the pressure inside the plastic syringe or the plastic cartridge. When the pre-filled syringes and cartridges are made of glass and the above-stated two requirements are met, they can be sterilized at an autoclave pressure that is less, equal to or greater than the pressure inside the glass syringes and cartridges.

In order to maintain an autoclave pressure that is less than the internal pressure of the syringes or cartridges, the vapor pressure of the content in the syringes and cartridges at the sterilization temperature must be determined. A pressure offset is then incorporated into programmable controls having hardware and software. Such control selectively adds air during the autoclave cycle to maintain a pressure in the autoclave that is lower than the pressure inside the syringes or cartridges. For example, if a formulation generates a vapor pressure of 15.2 psig at 121.5° C., the pressure in the autoclave chamber would be reduced to less than 15.2 psig. Examples of vapor pressure of some samples are as follows:

| Example | Sterilization Temp | Vapor Pressure, psig |
|---|---|---|
| Purified Water | 121.5° C. | 15.2 |
| Iohexol Solution 75.5% w/v | 121.5° C. | 14.7 |
| Iohexol Solution 51.77% w/v | 121.5° C. | 15.0 |

To provide the necessary control system, programmable autoclaves are commercially available (American Sterilizer Co., PA) to accomplish such controls using a temperature measuring device, such as a thermocouple, RTD or a pressure transducer, in direct contact with the content of the syringe to continuously feed data into the computer and trigger the necessary response thereto.

In the practice of the invention, when sterilizing a large number of samples in a batch-type operation, at least one temperature/pressure measuring device in direct contact with the content of one sample is necessary for monitoring the temperature and to automatically trigger a response to regulate the pressure within the autoclave. For that purpose a special syringe can be adapted which in all aspects is the same as any other syringe or cartridge, except for a built-in thermocouple, resistance temperature device (RTD) or pressure transducer connected to the hardware/software of the autoclave. Preferably, however, a statistically representative number of samples, placed at pre-determined location in the autoclave chamber, equipped with such temperature/pressure measuring device should be used.

BRIEF DESCRIPTION OF THE DRAWINGS

The accompanying drawings illustrate embodiments of the present invention in which:

FIG. 1. is a plan view of a hypodermic needle;

FIG. 2 is a plan view of a cartridge;

FIG. 3 is a plan view of a cap or sheath to cover the hypodermic needle shown in FIG. 1;

FIG. 4 is a plan view of a plunger or piston adopted for use in the cartridge shown in FIG. 2;

DETAILED DESCRIPTION OF THE INVENTION

Figure 5:
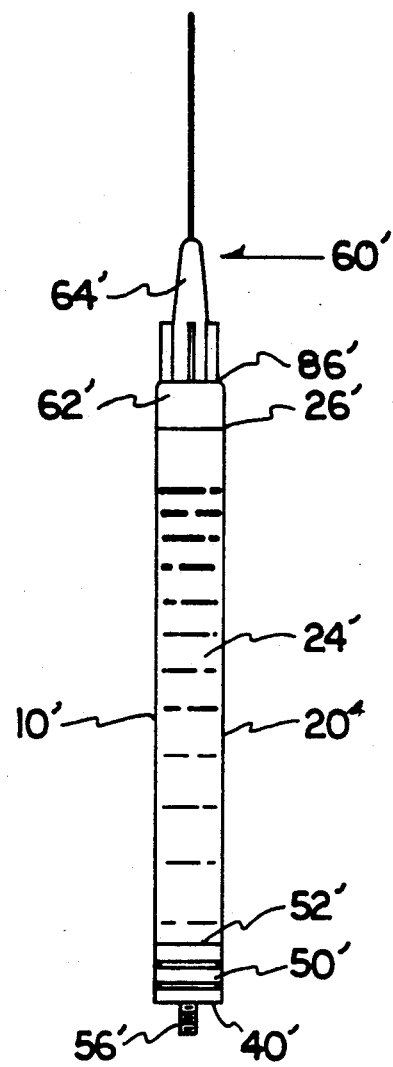
FIG. 5 is a plan view of a fully assembled syringe; hypodermic needle and plunger.

The invention will now be described in detail with reference to the foregoing figures where like numerals are used to identify like parts.

Referring to the drawings, there are illustrated two embodiments of the present invention: FIG. 2 shows a cartridge and FIG. 5 shows a syringe with an attached hypodermic needle.

Shown in FIG. 2, cartridge 10 comprises: a cartridge barrel 20, formed of glass or plastic having a distal end 26 and a proximal end 40. Distal end 26 has a neck portion 28 which terminates in an opening (not shown) closed by a diaphragm cap 30 and a diaphragm 36. Diaphragm cap 30 contains an annular groove 32 to receive a snap-on hypodermic needle 60 shown in FIG. 1. Hypodermic needle 60 comprises a snap-on portion 62 which is to engage diaphragm cap 30 in a mating relationship; and a conical portion 64 which is to receive and engage proximal end 74 of cap 70. When the hypodermic needle 60 is snapped on the cartridge, the proximal end of said needle pierces the diaphragm 36 thereby providing communication between said needle and the liquid medicament 24 contained in cartridge barrel 20. The proximal end 40 of the cartridge 10 is open for receipt of a plunger or piston 50, shown in FIG. 4, which has a forward, liquid-interfacing surface 52 and a rearwardly extending threaded portion 56 for interconnection with a plunger rod (not shown) when the cartridge is readied for use. Cartridge barrel 20 is filled with a liquid medicament 24 in such a way that: (1) a head space of no more than about 10% of the volume of the liquid is provided at the distal end 26 of the cartridge barrel 20 and; (2) at the proximal end 40 of the cartridge barrel 20 sufficient leeway is provided for the plunger to slide toward the proximal end in response to the thermal expansion of the liquid formulation contained in the cartridge 10. Such leeway should be about 10% or more of the volume of the liquid formulation. To insure against accidental pricking, and to protect the hypodermic needle 60 from contamination and damage, a cap or sheath 70 is provided, as shown in FIG. 3. Said cap 70 comprises a closed distal end 72 and an open proximal end 74 which is adopted to engage the conical portion 64 of hypodermic needle 60. The hypodermic needle and cap for the same may be fitted to the cartridge after the terminal sterilization process is complete.

FIG. 5 shows a syringe 10' equipped with a hypodermic needle 60' and plunger 50', and filled with a liquid medicament 24'. Syringe 10' comprises: a syringe barrel 20', formed of glass or plastic, having a distal end 26' and a proximal end 40'. Hypodermic needle 60' comprises a conical portion 64' which is to receive and engage proximal end 74 of cap 70 shown in FIG. 3. Plunger 50', having a liquid interfacing surface 52' and a rearwardly extending threaded portion 56' for interconnection with a plunger rod, is shown inserted into syringe barrel 20' at its proximal end 40'. The syringe functions analogously to the cartridge hereinbefore described. It is important here as well as with the cartridges, that syringe barrel 20' is filled with a liquid medicament 24' in such a way that: (1) a head space of no more than about 10% is provided at the distal end 26' of the syringe barrel 20' and; (2) at the proximal end 40' of the syringe barrel 20' sufficient leeway is provided for the plunger to slide toward the proximal end in response to the thermal expansion of the liquid formulation contained in syringe 10'. Such leeway should be about 10% or more of the volume of the liquid formulation.

Figure 6:
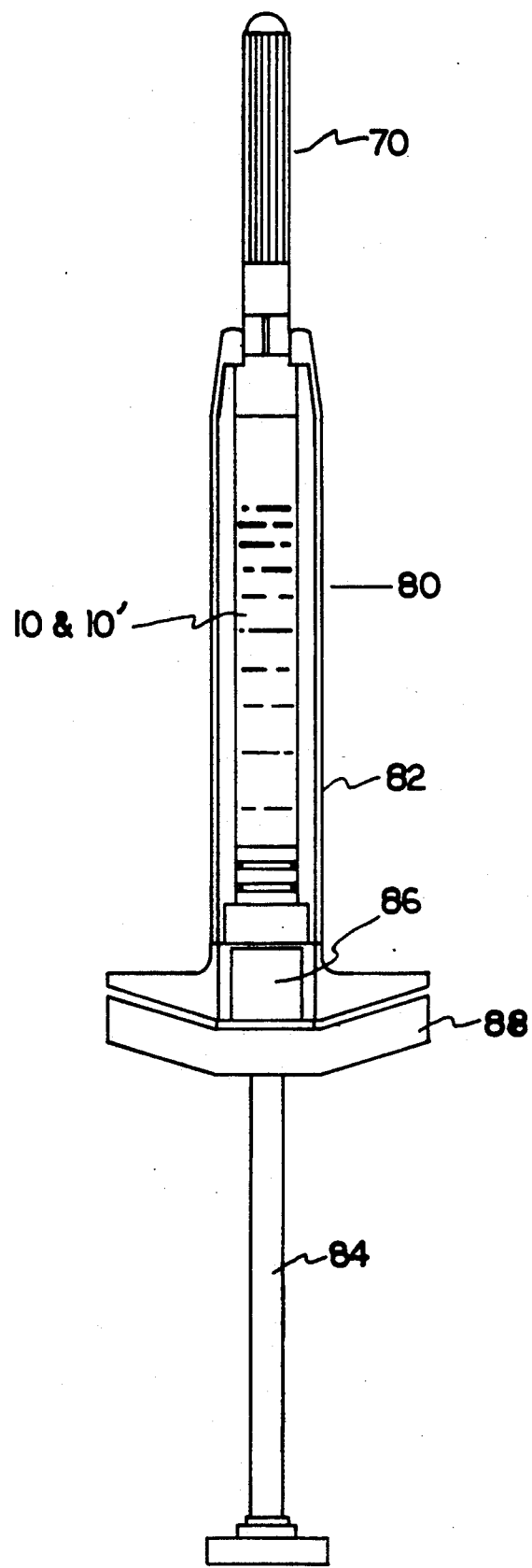
FIG. 6 is a plan view of a syringe holder having the cap, shown in FIG. 3, thereon.

The cartridge and syringe containing the liquid medicament therein, hereinbefore described, are sterilized according to the method of the present invention and are used in the conventional manner to administer their content to a patient. A convenient way to accomplish such administration is by the use of a syringe/cartridge holder, such as shown in FIG. 6. A similar holder is disclosed in U.S. Pat. No. 4,585,445, and is incorporated herein by reference. The syringe/cartridge holder 80 comprises a semi-cylindrical body portion 82, a plunger rod 84, associated piston engagement means 86 and finger gripping means 88. Semi-cylindrical body portion 82 is adapted for sideloading a cartridge 10 or syringe 10' through the open side wall. The cartridge/syringe is then locked in the holder to prevent axial displacement thereof, and plunger rod 84 is engaged with plunger 56 of the cartridge (or 56' of the syringe) through piston engagement means 86. After removal of cap 70, the assembly is ready for aspirating use.

The present terminal sterilization method may be used for a variety of chemical, pharmaceutical and veterinary liquid formulations, including liquid contrast media, and is an important advance in providing pyrogen/bacteria/viral free sterile products.

While preferred embodiments of the invention have been described and illustrated in the specification and drawings, it is to be understood that such is merely illustrative of the underlying concept and features of the invention and are not to be limiting of the scope of the invention and the appended claims.

What is claimed is:

1. A method for terminal sterilization of a pre-filled plastic syringe comprising: providing
   a syringe barrel terminating in a nozzle at a distal end of the syringe barrel, and an open or proximal end and
   a slideable plunger situated in the syringe barrel sealing the proximal end of the syringe barrel to retain a liquid therein and having a means to engage a plunger rod;
   inserting the slideable plunger into the syringe barrel and sliding it toward the distal end thereof to leave a volume of at least about 2% empty space between the slideable plunger and the proximal end of the syringe barrel;
   filling the syringe barrel through the nozzle of the syringe barrel with the liquid allowing for a head space not exceeding 10% by volume;
   hermetically sealing the nozzle by a cap;

placing the pre-filled plastic syringe into an autoclave chamber to sterilize the liquid therein, said pre-filled plastic syringe having a pressure on outside surfaces of the pre-filled plastic syringe exerted by a steam atmosphere in the autoclave chamber and an internal pressure of the liquid contained in the pre-filled plastic syringe;

autoclaving the pre-filled plastic syringe at an autoclave pressure less than the pressure of the liquid in the pre-filled plastic syringe; and cooling the autoclave chamber with a water cascade or nozzle spray or air draft at a rate that will not allow a collapse of the steam atmosphere in the autoclave chamber.

2. The method of claim 1 wherein said plastic syringe is filled with said liquid allowing essentially no head space.

3. The method of claim 1 wherein the volume of empty space between the slideable plunger and the proximal end of the syringe barrel is 5%.

4. The method of claim 3 wherein the volume of empty space between the slideable plunger and the proximal end of the syringe barrel is 10%.

5. The method of claim 1 wherein said slideable plunger is constructed and arranged to move toward the proximal end of the syringe barrel in response to thermal expansion and vapor pressure of the liquid contained therein.

6. The method of claim 1 wherein the internal pressure in the pre-filled plastic syringe is continuously monitored during autoclave cycles and the pressure in the autoclave chamber is kept at least one unit of pressure controllability lower than the internal pressure of the pre-filled plastic syringe.

7. The method of claim 1 wherein said liquid is a liquid medicament.

8. The method of claim 1 wherein said liquid is a liquid contrast agent used for diagnostic examination.

9. A method for terminal sterilization of a pre-filled plastic cartridge comprising: providing a cartridge barrel terminating in a neck portion at a distal end of the cartridge barrel constructed and arranged to receive a pierceable diaphragm, and an open or proximal end and a slideable plunger situated in the cartridge barrel sealing the proximal end of the cartridge barrel to retain a liquid therein and having a means to engage a plunger rod;

inserting the slideable plunger into the cartridge barrel and positioning the slideable plunger to leave a volume of at least 2% empty space between the slideable plunger and the proximal end of the cartridge barrel;

filling the cartridge barrel with the liquid through the distal end of the cartridge barrel allowing for a head space not exceeding 10% by volume;

hermetically sealing the distal end by a pierceable diaphragm; placing the pre-filled plastic cartridge into an autoclave chamber to sterilize the liquid therein, said pre-filled plastic cartridge having a pressure on the outside surfaces of the pre-filled plastic cartridge exerted by a steam atmosphere in the autoclave chamber and an internal pressure of the liquid contained in the pre-filled plastic cartridge; and autoclaving the pre-filled plastic cartridge at an autoclave pressure less than the pressure of the liquid in the pre-filled plastic cartridge at a rate that will not allow a collapse of the steam atmosphere in the autoclave chamber.

10. The method of claim 9 wherein said plastic cartridge is filled with said liquid allowing essentially no head space.

11. The method of claim 9 wherein the volume of empty space between the slideable plunger and the proximal end of the cartridge barrel is 5%.

12. The method of claim 11 wherein the volume of empty space between the slideable plunger and the proximal end of the cartridge barrel is 10%.

13. The method of claim 9 wherein said slideable plunger is constructed and arranged to move toward the proximal end of the cartridge barrel in response to thermal expansion and vapor pressure of the liquid contained therein.

14. The method of claim 9 wherein the internal pressure of the pre-filled plastic cartridge is continuously monitored during autoclave cycles and the pressure in the autoclave chamber is kept at least one unit of pressure controllability lower than the internal pressure of the pre-filled plastic cartridge during cooldown.

15. The method of claim 9 wherein said liquid is a liquid medicament.

16. The method of claim 9 wherein said liquid is a liquid contrast agent used for diagnostic examination.

17. A method for terminal sterilization of a pre-filled glass syringe comprising: providing a syringe barrel terminating in a nozzle at a distal end of the syringe barrel, and an open or proximal end and a slideable plunger situated in the syringe barrel sealing the proximal end of the syringe barrel to retain a liquid therein and having a means to engage a plunger rod;

inserting the slideable plunger into the syringe barrel and sliding it toward the distal end thereof to leave a volume of at least about 2% empty space between the slidable plunger and the proximal end of the syringe barrel;

filling the syringe barrel through the nozzle of the syringe barrel with the liquid allowing for a head space not exceeding 10% by volume;

hermetically sealing the nozzle by a cap;

placing the pre-filled glass syringe into an autoclave chamber to sterilize the liquid therein, said pre-filled glass syringe having a pressure on outside surfaces of the pre-filled glass syringe exerted by a steam atmosphere in the autoclave chamber and an internal pressure of the liquid contained in the pre-filled glass syringe;

autoclaving the pre-filled glass syringe at an autoclave pressure less than the pressure inside the pre-filled glass syringe; and cooling the autoclave chamber with a water cascade or nozzle spray or air draft at a rate that will not allow a collapse of the steam atmosphere in the autoclave chamber.

18. The method of claim 17 wherein said glass syringe is filled with said liquid allowing essentially no head space.

19. The method of claim 17 wherein the volume of empty space between the slideable plunger and the proximal end of the syringe barrel is 5%.

20. The method of claim 19 wherein the volume of empty space between the slideable plunger and the proximal end of the syringe barrel is 10%.

21. The method of claim 17 wherein said slideable plunger is constructed and arranged to move toward the proximal end of the syringe barrel in response to thermal expansion and vapor pressure of the liquid contained therein.

22. The method of claim 17 wherein said liquid is a liquid medicament.

23. The method of claim 17 wherein said liquid is a liquid contrast agent used for diagnostic examination.

24. A method for terminal sterilization of a pre-filled glass cartridge comprising: providing a cartridge barrel terminating in a neck portion at a distal end of the cartridge barrel constructed and arranged to receive a pierceable diaphragm, and an open or proximal end and a slideable plunger situated in the cartridge barrel sealing the proximal end of the cartridge barrel to retain a liquid therein and having a means to engage a plunger rod;

inserting the slideable plunger into the cartridge barrel and positioning it to leave a volume of at least 2% empty space between the slideable plunger and the proximal end of the cartridge barrel;

filling the cartridge barrel with the liquid through the distal end of the cartridge barrel allowing for a head space not exceeding 10% by volume;

hermetically sealing the distal end by a pierceable diaphragm;

placing the pre-filled glass cartridge into an autoclave chamber to sterilize the liquid therein, said pre-filled glass cartridge having a pressure on outside surfaces of the pre-filled glass cartridge exerted by a steam atmosphere in the autoclave chamber and an internal pressure of the liquid contained in the pre-filled glass cartridge;

autoclaving the pre-filled glass cartridge at an autoclave pressure that is less than the pressure inside the pre-filled glass cartridge; and cooling the autoclave chamber with a water cascade or nozzle spray or air draft at a rate that will not allow a collapse of the steam atmosphere in the autoclave chamber.

25. The method of claim 24 wherein said glass cartridge is filled with said liquid allowing essentially no head space.

26. The method of claim 24 wherein the volume of empty space between the slideable plunger and the proximal end of the cartridge barrel is 5%.

27. The method of claim 26 wherein the volume of empty space between the slideable plunger and the proximal end of the cartridge barrel is 10%.

28. The method of claim 24 wherein said slideable plunger is constructed and arranged to move toward the proximal end of the cartridge barrel in response to thermal expansion and vapor pressure of the liquid contained therein.

29. The method of claim 24 wherein said liquid is a liquid medicament.

30. The method of claim 24 wherein said liquid is a liquid contrast agent used for diagnostic examination.

* * * * *